US010918686B2

(12) United States Patent
Siurkus

(10) Patent No.: US 10,918,686 B2
(45) Date of Patent: Feb. 16, 2021

(54) OLEO GEL COMPOSITION AND DELIVERY SYSTEM WITH ACTIVE COMPOUNDS FROM CANNABIS SATIVA AND MENTHA ARVENSIS FOR REDUCTION OF INFLAMMATION AND PAIN IN DEEP TISSUES

(71) Applicant: UAB SATIMED, Utena (LT)

(72) Inventor: Juozas Siurkus, Kaisiadorys (LT)

(73) Assignee: UAB Satimed, Vilnius (LT)

( * ) Notice: Subject to any disclaimer, the term of this patent is extended or adjusted under 35 U.S.C. 154(b) by 169 days.

(21) Appl. No.: 16/093,149

(22) PCT Filed: Apr. 7, 2017

(86) PCT No.: PCT/IB2017/052004
§ 371 (c)(1),
(2) Date: Oct. 12, 2018

(87) PCT Pub. No.: WO2017/178937
PCT Pub. Date: Oct. 19, 2017

(65) Prior Publication Data
US 2019/0167749 A1 Jun. 6, 2019

(30) Foreign Application Priority Data
Apr. 13, 2016 (LT) ..................... 2016 046

(51) Int. Cl.
| *A61K 36/63* | (2006.01) |
| *A61K 36/534* | (2006.01) |
| *A61K 9/00* | (2006.01) |
| *A61K 9/06* | (2006.01) |
| *A61K 47/00* | (2006.01) |
| *A61K 31/352* | (2006.01) |
| *A61K 36/185* | (2006.01) |
| *A61K 47/44* | (2017.01) |
| *A61P 19/02* | (2006.01) |
| *A61P 25/04* | (2006.01) |
| *A61P 29/00* | (2006.01) |
| *A61K 31/192* | (2006.01) |
| *A61K 47/02* | (2006.01) |

(52) U.S. Cl.
CPC .............. *A61K 36/63* (2013.01); *A61K 9/00* (2013.01); *A61K 9/0014* (2013.01); *A61K 9/06* (2013.01); *A61K 31/192* (2013.01); *A61K 31/352* (2013.01); *A61K 36/185* (2013.01); *A61K 36/534* (2013.01); *A61K 47/00* (2013.01); *A61K 47/02* (2013.01); *A61K 47/44* (2013.01); *A61P 19/02* (2018.01); *A61P 25/04* (2018.01); *A61P 29/00* (2018.01); *A61K 2236/37* (2013.01)

(58) Field of Classification Search
None
See application file for complete search history.

(56) References Cited

U.S. PATENT DOCUMENTS

| 6,328,992 B1 * | 12/2001 | Brooke ................ A61K 31/352 424/449 |
| 6,949,582 B1 | 9/2005 | Wallace |
| 2009/0247619 A1 * | 10/2009 | Stinchcomb ............. A61K 9/06 514/454 |
| 2012/0264818 A1 | 10/2012 | Newland |

FOREIGN PATENT DOCUMENTS

| EP | 1186298 B1 | 3/2002 |
| FR | 2 973 706 A1 | 10/2012 |

OTHER PUBLICATIONS

Baoge, L., E. Van Den Steen, S. Rimbaut, N. Philips, E. Witvrouw, K. F. Almqvist, G. Vanderstraeten, and L. C. Vanden Bossche. 2012. "Treatment of Skeletal Muscle Injury: A Review." ISRN Orthopedics 2012: 689012. doi:10.5402/2012/689012.

Bondesen, Brenda A., Stephen T. Mills, Kristy M. Kegley, and Grace K. Pavlath. 2004. "The COX-2 Pathway Is Essential during Early Stages of Skeletal Muscle Regeneration." American Journal of Physiology. Cell Physiology 287 (2): C475-83. doi:10.1152/ajpcell.00088.2004.

Fisar, Zdenek. 2009. "Phytocannabinoids and Endocannabinoids." Current Drug Abuse Reviews 2 (1): 51-75.

Fogh, Karsten, Troels Herlin, and Knud Kragballe. 1989. "Eicosanoids in Skin of Patients with Atopic Dermatitis: Prostaglandin E 2 and Leukotriene B 4 Are Present in Biologically Active Concentrations." Journal of Allergy and Clinical Immunology 83 (2): 450-55.

Hampson, A. J., M. Grimaldi, J. Axelrod, and D. Wink. 1998. "Cannabidiol and (-)Delta9-Tetrahydrocannabinol Are Neuroprotective Antioxidants." Proc Natl Acad Sci U S A 95 (14): 8268-73.

Hassan, Samia, Khalil Eldeeb, Paul J. Millns, Andrew J. Bennett, Stephen P. H. Alexander, and David A. Kendall. 2014. "Cannabidiol Enhances Microglial Phagocytosis via Transient Receptor Potential (TRP) Channel Activation." Br J Pharmacol 171 (9): 2426-39. doi:10.1111/bph.12615.

Izzo, Angelo A., Francesca Borrelli, Raffaele Capasso, Vincenzo Di Marzo, and Raphael Mechoulam. 2009. "Non-Psychotropic Plant Cannabinoids: New Therapeutic Opportunities from an Ancient Herb." Trends Pharmacol Sci 30 (10): 515-27. doi:10.1016/j.tips. 2009.07.006.

Maccarrone, M., and A. Finazzi-Agro. 2003. "The Endocannabinoid System, Anandamide and the Regulation of Mammalian Cell Apoptosis." Cell Death & Differentiation 10 (9): 946-55.

(Continued)

*Primary Examiner* — Russell G Fiebig
(74) *Attorney, Agent, or Firm* — AAA Law; Shannon K. Stauffer

(57) ABSTRACT

Disclosed is an oleo gel composition including essential combination of synergistically acting phyto-active materials, non-psychotropic phytocannabinoids from the plant of *Cannabis sativa*: Cannabidiol, Cannabidiolic acid, Cannabivarin and Cannabigerol in combination with extract of Olive *europaea* Fruit Oil, *Mentha arvensis* leaf oil, and Silica colloidal anhydrous ensuring the delivery of cannabinoids to the deep tissues in order to reduce pain and inflammation of skeletal muscles and joints caused by trauma or/and induced by arthritis/osteoarthritis.

9 Claims, 1 Drawing Sheet

(56) References Cited

OTHER PUBLICATIONS

Malfait, A. M., R. Gallily, P. F. Sumariwalla, A. S. Malik, E. Andreakos, R. Mechoulam, and M. Feldmann. 2000. "From the Cover: The Nonpsychoactive Cannabis Constituent Cannabidiol Is an Oral Anti-Arthritic Therapeutic in Murine Collagen-Induced Arthritis." Proceedings of the National Academy of Sciences of the United States of America 97 (17):9561. doi:10.1073/pnas.160105897.

Nderitu, Paul, Lucy Doos, Peter W. Jones, Simon J. Davies, and Umesh T. Kadam. 2013. "Non-Steroidal Anti-Inflammatory Drugs and Chronic Kidney Disease Progression: A Systematic Review." Family Practice 30 (3): 247-55. doi:10.1093/fampra/cms086.

Neogi, Tuhina, and Yuqing Zhang. 2013. "Epidemiology of OA." Rheumatic Diseases Clinics of North America 39 (1): 1. doi:10.1016/j.rdc.2012.10.004.

Pertwee, R. G. 2008. "The Diverse CB1 and CB2 Receptor Pharmacology of Three Plant Cannabinoids: delta9-Tetrahydrocannabinol, Cannabidiol and delta9-Tetrahydrocannabivarin." Br J Pharmacol 153 (2): 199-215. doi:10.1038/sj.bjp.0707442.

Rainsford, K. D., S. C. Roberts, and S. Brown. 1997. "Ibuprofen and Paracetamol: Relative Safety in Non-prescription Dosages." Journal of Pharmacy and Pharmacology 49 (4): 345-76. doi:10.1111/j.2042-7158.1997.tb06809.x.

Ramer, Robert, Katharina Heinemann, Jutta Merkord, Helga Rohde, Achim Salamon, Michael Linnebacher, and Burkhard Hinz. 2013. "COX-2 and PPAR-γ Confer Cannabidiol-Induced Apoptosis of Human Lung Cancer Cells." Mol Cancer Ther 12 (1): 69-82. doi:10.1158/1535-7163.MCT-12-0335.

Roth, Dr Sanford H. 2012. "Coming to Terms with Nonsteroidal Anti-Inflammatory Drug Gastropathy." Drugs 72 (7): 873-79. doi:10.2165/11633740-000000000-00000.

Ryan, Duncan, Alison J. Drysdale, Carlos Lafourcade, Roger G. Pertwee, and Bettina Platt. 2009. "Cannabidiol Targets Mitochondria to Regulate Intracellular Ca2+ Levels." J Neurosci 29 (7): 2053-63. doi:10.1523/UNEUROSCI.4212-08.2009.

Schneider, Christian. 2011. "Traumeel—an Emerging Option to Nonsteroidal Anti-Inflammatory Drugs in the Management of Acute Musculoskeletal Injuries." International Journal of General Medicine 4: 225-34. doi:10.2147/IJGM.S16709.

Schwitzer, Thomas, Raymund Schwan, Karine Angioi-Duprez, Isabelle Ingster-Moati, Laurence Lalanne, Anne Giersch, and Vincent Laprevote. 2015. "The Cannabinoid System and Visual Processing: A Review on Experimental Findings and Clinical Presumptions." Eur Neuropsychopharmacol 25 (1): 100-112. doi:10.1016/j.euroneuro.2014.11.002.

Shen, Wei, Yong Li, Ying Tang, James Cummins, and Johnny Huard. 2005. "NS-398, a Cyclooxygenase-2-Specific Inhibitor, Delays Skeletal Muscle Healing by Decreasing Regeneration and Promoting Fibrosis." The American Journal of Pathology 167 (4): 1105-17. doi:10.1016/S0002-9440(10)61199-6.

Shen, Wei, Victor Prisk, Yong Li, William Foster, and Johnny Huard. 2006. "Inhibited Skeletal Muscle Healing in Cyclooxygenase-2 Gene-Deficient Mice: The Role of PGE2 and PGF2alpha." Journal of Applied Physiology (Bethesda, Md.: 1985) 101 (4): 1215-21. doi:10.1152/japplphysiol.01331.2005.

Shrivastava, Amit Kumar, and Aparna Pandey. 2012. "Inflammation and Rheumatoid Arthritis." Journal of Physiology and Biochemistry 69 (2): 335-47. doi:10.1007/s13105-012-0216-5.

Smith, L. L., A. Anwar, M. Fragen, C. Rananto, R. Johnson, and D. Holbert. 2000. "Cytokines and Cell Adhesion Molecules Associated with High-Intensity Eccentric Exercise." European Journal of Applied Physiology 82 (1-2): 61-67. doi:10.1007/s004210050652.

Sumariwalla, Percy F., Ruth Gallily, Susanna Tchilibon, Ester Fride, Raphael Mechoulam, and Marc Feldmann. 2004. "A Novel Synthetic, Nonpsychoactive Cannabinoid Acid (HU-320) with Antiinflammatory Properties in Murine Collagen- Induced Arthritis." Arthritis & Rheumatism 50 (3): 985-98. doi:10.1002/art.20050.

Takeda, Shuso. 2013. "[Medicinal chemistry and pharmacology focused on cannabidiol, a major component of the fiber-type cannabis]." Yakugaku Zasshi: Journal of the Pharmaceutical Society of Japan 133 (10): 1093-1101.

van der Stelt, Mario, and Vincenzo Di Marzo. 2005. "Anandamide as an Intracellular Messenger Regulating Ion Channel Activity." Prostaglandins Other Lipid Mediat 77 (1-4): 111-22. doi:10.1016/j.prostaglandins.2004.09.007.

International Search Report, dated Jul. 25, 2017, from corresponding PCT/IB2017/052004 application.

* cited by examiner

OLEO GEL COMPOSITION AND DELIVERY SYSTEM WITH ACTIVE COMPOUNDS FROM CANNABIS SATIVA AND MENTHA ARVENSIS FOR REDUCTION OF INFLAMMATION AND PAIN IN DEEP TISSUES

FIELD OF THE INVENTION

Present invention relates to oleo gel compositions comprising phytocannabinoids from the plant *Cannabis sativa* for reduction of pain and post traumatic inflammation and/or arthritis/osteoarthritis (OA) in the deep tissues of joints and muscles.

BACKGROUND OF THE INVENTION

The inflammation mechanism of deep muscle and/or skeletal tissues resulted by trauma and osteoarthritis (OA) is related to the metabolism of arachidonic acid by cyclooxygenases (COX1 and COX 2) and or by lipoxygenase which produces regulatory molecules eicosanoids: prostaglandins or thromboxanes and leukotrienes respectively (see section below). The treatment of post-traumatic inflammation and OA is based on therapy using nonsteroidal anti-inflammatory drugs (NSAIDs) and/or synthetic corticosteroids, which can be used orally or/and topically. The intensive consumption of NSAIDs and corticosteroids can cause side effects, such as lesions of gastrointestinal track, renal and cardiac systems (Nderitu et al. 2013) (Rainsford, Roberts, and Brown 1997) (Roth 2012).

Herein provided invention describes a topical composition in the form of oleo gel comprising essential combination of synergistically acting phyto-active materials, non-psychotropic phytocannabinoids from the plant *Cannabis sativa*: Cannabidiol (CBD), Cannabidiolic acid (CBDA), Cannabivarin (CBV), and Cannabigerol (CBG) in combination with a matrix for delivery of cannabinoids to the deep tissues in order to reduce pain and inflammation of skeletal muscles and joints caused by trauma or/and induced by arthritis/osteoarthritis (OA). Differently from NSAIDs and synthetic corticosteroids there are no published data, to this date, which would describe pharmacological side effects or lesions caused by natural phytocannabinoids. Therefore the present invention can substitute or complement a therapy based on synthetic NSAIDs and corticosteroids for reduction of inflammation lesions in the deep tissues of skeletal system.

Pharmacological features of cannabinoids. Centuries ago the extracts of *Cannabis sativa* plant were used as pain relievers and anti-inflammatory agents. Currently, the topic of pharmacological features of cannabinoids became a great research focus and it is rapidly growing. The increasing research focus on the naturally occurring therapeutic value possessing phyto-compounds such as cannabinoids, could be explained by the fact that many of the synthetic medical drugs lack therapeutic efficiency or/and may induce drastic side effects. The *C. sativa* contains 3 major classes of bioactive molecules: flavonoids, terpenoids and phytocannabinoids. The family of phytocannabinoids compromises approximately 60 types of terpenophenolic compounds, which are the most important chemicals in the *C. sativa* plant, possessing highest therapeutic value. Phytocannabinoids are the only natural analogues of the mammal endocannabinoids. Phytocannabinoids are accumulated in the glandular structures of cannabis plants, known as trichomes. Depending on the species, cannabis can accumulate Δ9-tetrahydrocannabinol (Δ9-THC) which is a major psychoactive ingredient and/or cannabidiols (CBD) which are non-psychoactive ingredients of cannabis plant (Fisar 2009). The most common, therapeutic value possessing, but non-psychoactive cannabinoids from *C. sativa* are Cannabidiol (CBD), Cannabionic acid (CBDA), Cannabichromene (CBC), Cannabicyclol (CBL), Cannabivarin (CBV), Cannabigerol (CBG), Tetrahydrocannabivarin (THCV), Cannabichromevarin (CBCV), Cannabigerovarin (CBGV), and Cannabigerol Monoethyl Ether (Fisar 2009). Family of non-psychoactive phytocannabinoids has a very low affinity towards CB1 and CB2—endocannabinoid system related receptors (Pertwee 2008). However, they modulate pharmacological effects by utilizing other endocannabinoid system related receptors, i.e. transient receptor potential (TRP) channels (Hassan et al. 2014), the peroxisome proliferators—activated receptor g (PPARg), GPR55, the putative abnormal-CBD receptor, 5-hydroxytryptamine receptor subtype 1A (5-HT1A), glycine a1 and a1b receptors, the adenosine membrane transporter phospholipase A2, lipoxygenase (LOX) and cyclooxygenase-2 (COX-2) enzymes (Izzo et al. 2009) and Ca2+ homeostasis regulation system (Ryan et al. 2009). For example, the phytocannabinoid based anti-inflammatory action occurs via inhibition of inflammatory COX-2 protein (Takeda et al. 2008), or inhibition of inactivation of endogenous cannabinoid anandamide, which is an intracellular messenger for regulation of ion channel activity (van der Stelt and Di Marzo 2005). In addition, CBD driven modulation of intracellular Ca2+ concentration is related to many therapeutic effects. For example, one of them is anticancer effect via generation of reactive oxygen species (ROS) for induction of apoptosis in cancer cells (Ramer et al. 2013). Cannabidiol and −Δ-9-tetrahydrocannabinol are neuroprotective antioxidants (Hampson et al. 1998). Within the human body the CB1 and CB2 receptors are interacting with the endogenous ligands—endocannabinoids, which should not be confused with their analogues—phytocannabinoids. The physiological action of endocannabinoids and psychoactive phytocannabinoids is driven via their interactions with the specific class of Gαi protein-coupled receptors known as a Central Cannabinoid Receptor (CB1) and Peripheral Cannabinoid Receptor (CB2), respectively. The highest abundance of CB1 is located in the central nervous system (basal ganglia, hippocampus, cerebellum and cortex), where they mediate cannabinoid related psychoactive effects. In addition, the CB1 receptors are present in the nerve-terminals of testis, uterus, vascular endothelium, eye, spleen, ileum, and in adipocytes. In addition, the CB2 receptors are distributed within the immune system of the body, in the enriched areas of B lymphocytes (Schwitzer et al. 2015). The molecules of endocannabinoids are interacting with CB1 and CB2 receptors via moieties of esters, ethers, long-chain polyunsaturated fatty acids and amides. The function of endocannabinoids is mainly related with regulation of various neurotransmitter release in the peripheral and neural tissues, regulation of fat and energy metabolism and they are also very important in inflammation processes. Therefore, the components of endocannabinoid system—CB1 and CB2 receptors and endogenous cannabinoids—are the targets for the treatment of neurodegenerative (Parkinson's, Alzheimer's and Huntington's) diseases, inflammatory pain, multiple sclerosis, glaucoma, neuropathic pain, obesity and oncological diseases (Maccarrone and Finazzi-Agro 2003).

Inflammation is a biological process during which arachidonic acid is released from the phospholipid-based cell membranes and metabolized by cyclooxygenases (COX1 and COX 2) to produce regulatory molecules eicosanoids: prostaglandins or thromboxanes. The second possibility for metabolism of the arachidonic acid is the pathway controlled by lipoxygenase (LOX) where the enzymatic reaction leads to production of regulatory molecules belonging to the family of the leukotrienes. Prostaglandins play a key role in the generation of the inflammatory response. Biosynthesis of prostaglandins is significantly increased in inflamed tissue and is contributing to the development of the cardinal signs of acute inflammation. Certain eicosanoids which are derived from arachidonic acid are potent mediators of skin inflammation and modulators of certain T-lymphocyte activities (Samuelsson 1990). The levels of the cyclooxygenase product, prostaglandin E2 (PGE2) and the lipoxygenase products, leukotriene B4 (LTB4), 12- and 15-hydroxyeicosatetraenoic acid, elevated in biopsy specimens obtained by keratome from lesional, perilesional, and patients with AD and psoriasis compared to clinically unaffected patients (Fogh, Herlin and Kragballe 1989).

Osteoarthritis (OA) is the leading cause of disability among the elderly population. The etiology, pathogenesis, and progression of OA are still not fully understood. OA has a multifactorial origin and is slowly progressive. The disease process can be described as degradation and loss of articular cartilage accompanied by hypertrophic bone changes, with osteophyte formation and subchondral plate thickening. The process includes changes in articular cartilage and surrounding bone, an imbalance in loss of cartilage (due to matrix degradation, and an attempt to repair this matrix) (Neogi and Zhang 2013). Osteoblasts—specialized mesenchymal cells produce prostaglandins via both COX-1 and COX-2 activities. Prostaglandins stimulate bone resorption by increasing the number and activity of osteoclasts, and PGE2 is the most potent agonist. The roles of a number of stimulators of formation of tartrate-resistant acid phosphatase-positive giant cells with osteoclast features are blocked by inhibiting endogenous prostaglandin synthesis. Prostaglandins also enhance bone formation by stimulating the replication and differentiation of osteoblasts with an increase in the production of growth factors. In fully differentiated osteoblasts, high concentrations of prostaglandins can inhibit collagen synthesis. Prostaglandins may also mediate the response to mechanical forces in bone, because bone formation stimulated by impact loading can be blocked by NSAIDs (Shrivastava and Pandey 2012).

The therapeutic potential of cannabinoids for treatment of arthritis. The therapeutic potential of cannabidiol (CBD), the major non-psychoactive component of cannabis, was already explored in murine collagen-induced arthritis (CIA). CIA was elicited by immunizing DBA/1 mice with type II collagen (CII) in complete Freund's adjuvant. The CII used was either bovine or murine, resulting in classical acute CIA or in chronic relapsing CIA, respectively. CBD was administered orally in both models of arthritis. The treatment effectively blocked progression of arthritis. CBD was equally effective when administered i.p. or orally. The dose dependency showed a bell-shaped curve, with an optimal effect at 5 mg/kg per day i.p. or 25 mg/kg per day orally. Clinical improvement was associated with protection of the joints against severe damage. Ex vivo, draining lymph node cells from CBD-treated mice showed a diminished CII-specific proliferation and IFN-gamma production, as well as a decreased release of tumour necrosis factor by knee synovial cells. In vitro effects of CBD included a dose-dependent suppression of lymphocyte proliferation, both mitogen-stimulated and antigen-specific, and the blockade of the Zymosan-triggered reactive oxygen burst by peritoneal granulocytes. It was also found that CBD administration was capable of blocking the lipopolysaccharide-induced rise in serum tumour necrosis factor in C57/BL mice. Taken together, this data shows that CBD, through its combined immunosuppressive and anti-inflammatory actions, has a potent anti-arthritic effect in CIA. In summary anti-inflammatory effect of cannabis compounds—CBD and CBDA is related to the selectivity to cyclooxygenase-2 (COX-2) and the CBD derivative, CBD-2',6'-dimethyl ether (CBDD), that exhibits inhibitory activity toward 15-lipoxygenase (15-LOX), an enzyme responsible for the production of oxidized low-density lipoprotein (LDL) (Malfait et al. 2000)(Sumariwalla et al. 2004)(Takeda 2013).

Injury of skeletal muscle, and especially mechanically induced damages such as contusion injury, frequently occurs in contact sports or domestic accidents. There are large variations with regard to injury severity and affected muscle group, as well as non-specificity of reported symptoms. The most important of these processes is post traumatic inflammation. The magnitude of the inflammatory response depends on two main factors, namely the severity of injury and the degree of vascularization of the tissue at the time of injury (Baoge et al. 2012). The early recovery phase is characterized by the overlapping processes of inflammation and occurrence of secondary damage. Although neutrophil infiltration has been named as a contributor to the latter, no clear evidence exists to support this claim. Macrophages, although forming part of the inflammatory response, have been shown to have a role in recovery, rather than in exacerbating secondary damage. Several probable roles for this cell type in the second phase of recovery, involving resolution processes, have been identified and include the following: (i) phagocytosis to remove cellular debris; (ii) switching from a pro- to anti-inflammatory phenotype in regenerating muscle; (iii) preventing muscle cells from undergoing apoptosis; (iv) releasing factors to promote muscle precursor cell activation and growth, and (v) secretion of cytokines and growth factors to facilitate vascular and muscle fibre repair. As a result of muscle injury and capillary rupture, blood-borne inflammatory cells and cytokines gain direct access to the site of injury.

In addition, although it is generally accepted that cytokines (e.g. tumour necrosis factor-a [TNFa], interleukin [IL]-1b and IL-6) are integral to the inflammatory response (Smith et al. 2000), in the early response to skeletal muscle injury, neutrophils are the most abundant immune cells at the injury site, but within the first 24 hours, neutrophil numbers start to decline and the number of macrophages increases (Li, Cummins, and Huard 2001). Nonsteroidal anti-inflammatory drugs (NSAIDs) are commonly prescribed for contusion injury, and many athletes use over-the-counter NSAIDs over long periods of time to reduce post-exercise pain and swelling (Schneider 2011). Although short-term NSAID treatment during the early repair phase (1-3 days) may result in a modest inhibition of inflammatory symptoms (swelling and pain), it may in fact have negative effects on the healing of the injured muscle if taken for a longer period (in excess of 3 days) (Almekinders 1999).

More direct evidence of immune involvement was reported in an animal model of contusion injury, where cyclo-oxygenase-2 (COX-2) inhibition by NSAID infusion was shown to result in faster restoration of microcirculation disrupted as a result of a mass-drop injury, thereby reducing skeletal muscle secondary tissue damage—measured in this study as leucocyte rolling and adhesion to the vascular endothelium. Although this seems to prove a positive effect of NSAIDs immediately after injury, other studies suggest that total inhibition of the inflammatory phase does not benefit the capacity for regeneration. For example, a study using myogenic precursor cells isolated from COX-2 knockout mice showed a decreased capacity for fusion of these cells in culture. This result is supported by an in vivo study, where a model of freeze injury was used. The results showed a decreased myofibre regeneration after long-term treatment with another COX-2 inhibitor. In summary the NSAID treatment does not have a negative effect on muscle recovery from injury if its use is limited to 3 days post-injury, but that long-term treatment has definite detrimental effects on speed of recovery. By taking into account the inflammatory actions of phytocannabinoids which are described above, the CBD and CBDA could be used as NSAIDs at the early phases of post injury skeletal muscles (Shen et al. 2005)(Shen et al. 2006)(Bondesen et al. 2004).

There are several examples of topical compositions comprising cannabidiol in combination with herbal extracts and can be dissolved in lipotropic solvent selected from a group consisting of triglycerides, hydrocarbons, alcohols, ketones, esters or ethers or they can be dissolved in the oil from *Cannabis sativa* seeds or they can be dissolved in hydrophilic solvent selected from the group consisting of aliphatic polar alcohols or their mixtures with water.

Document U.S. Pat. No. 6,949,582B1 describes the method of relieving analgesia and reducing inflammation based on composition containing from about 97.5% to about 99.5% by weight a 70% monohydric alcohol solution, and from about 0.5% to about 2.5% by weight of a synergistic cannabinoid mixture extracted from the female plant *Cannabis sativa* L, including in combination: 9-Tetrahydrocannabinol (delta-9-THC), 9-THC Propyl Analogue (THC-V), Cannabidiol (CBD), Cannabidiol Propyl Analogue (CBD-V), Cannabinol (CBN), Cannabichromene (CBC), Cannabichromene Propyl Analogue (CBC-V), Cannabigerol (CBG), terpenoids, and flavonoids. The liniment is applied topically, preferably by spraying, and the constituents of the mixture are absorbed through the skin and interact with cannabinoid receptors in the body and tissues of a human patient to produce therapeutic analgesic and anti-inflammatory effects without undesirable psychotropic side effects.

The presented composition is very different from the composition of herein presented invention, due to differences in the formulation—matrix, thickening agents, solubilising agents, active materials. Furthermore, the U.S. Pat. No. 6,949,582B1 composition comprises a dominating THC which is euphoric and can cause side effects—dizziness, psychosis, etc.

Document US20120264818A1—Topical Compositions with Cannabis Extracts invention discloses a method of making a topical composition for the treatment of pain. The topical composition includes a heat-treated cannabis material in a carrier. The carrier is typically an aprotic solvent that serves as both an extraction solvent and a skin penetrator. The topical composition may be applied, for example, directly to the skin or through a patch, strip, bandage, or covering. Suitable preservatives, antioxidants, and chemical stabilizers include, for example, alcohol, benzyl alcohol, butylated hydroxyanisole, butylparaben, calcium acetate, castor oil, chlorocresol, 4-chloro-m-cresol, citric acid, disodium edetate, edetate disodium, ethoxylated alcohol, ethyl alcohol, glycerin, methylparaben, parabens, potassium sorbate, propyl gallate, propylene glycol, propylparaben, sodium bisulfite, sodium citrate, sodium metabisulfite, sorbic acid, tannic acid, triglycerides of saturated fatty acids, zinc stearate, and combinations thereof. Suitable thickening, stiffening and suspending agents include, for example, aluminum stearate, beeswax, synthetic beeswax, carbomer 934, carbomer 934P, carbomer 940, cetostearyl alcohol, cetyl alcohol, cetyl esters wax, dextrin, glyceryl monostearate, hydroxypropyl cellulose, kaolin, paraffin, petrolatum, polyethylene, propylene glycol stearate, starch, stearyl alcohol, wax, white wax, xanthan gum, bentonite, and combinations thereof. In one embodiment, the topical composition is used to treat pain, inflammation, muscle tightness, muscle spasms, skin ulcerations, and scleroderma. In one embodiment, the topical composition is used to treat joint pain, muscle pain, or arthritis. The topical compositions, as described herein, may also include one or more optional ingredients, for example, palliative agents, skin conditioning agents, emollients, humectants, odorants, preservatives, solvents, thickening, stiffening and suspending agents, other agents, or a combination thereof. Other optional agents may be added to the composition including, for example, aloe, arachis oil, benzoic acid, cocoa butter, coenzyme Q10, Q10, dimethicone, eucalyptus oil, resorcinol, retinol, retinyl palmitate, retinyl acetate, fennel extract, whey protein, ceramide, silicone, alpha-hydroxy acids, beta-hydroxy acids, sorbitol, vitamin A, vitamin B, vitamin C, vitamin D, vitamin E.

The reference discloses a topical composition for treating pain (joint pain, arthritis, etc.) comprising cannabis extracts. However, olive oil and mint oil is not mentioned, silica is not listed as suitable thickening agent. The described composition comprises heat treated cannabis extract in which all anti-inflammatory compounds will be decarboxylated thus the pharmacological features of these cannabinoids will be lost or altered. The ratio between cannabinoids is not described as an essential to have a synergetic anti-inflammatory effect. The composition comprises synthetic alcohols, esters, waxes and other compounds which could have side effects such as skin irritation.

Document EP1186298B1 describes Structures and methods for administering cannabis to patients, where cannabis formulation is prepared with a total of 10 percent of a selected cannabinoid mixture in the drug formulation (comprising delta 8 THC 3%, delta 9 THC 30%, and cannabidiol 35% and cannabinol 32%). The cannabinoids are dispersed in the USP grade light mineral oil (Penta Mfg.), and a mixture of N,N-dimethyl amide (Hallcomid M 8-10) and linear alcohol ethoxylate (Rexonic® N4) in equal proportion (total of 20% of formulation) is dispersed also in the formulation. The formulation is then gelled for ease of processing by using silica particles (3% of formulation) (Spectrum Lab. Products). The permeation enhancing compounds are incorporated to increase skin permeability to the cannabinoids and to control the flux of cannabinoids through the skin.

"Cannabis", as used herein, means a cannabis solution which has been preferably extracted from its natural source such as marijuana and hashish, or any one or more compound or chemical component thereof, including tetrahydrocannabinol (THC), cannabinol (CBN), cannabidiol (CBD) and cannabichromene (CBC). As used herein, the term "oil" comprises any one or mixture of pharmaceutical grade light mineral oils, vegetable oils, fish and animal oils. Examples of vegetable oils are sesame, corn cottonseed, almond, orange, lemon, eucalyptus, olive, peanut, safflower, cinnamon, clove, and soybean. Other usable oils are cod liver and castor oils. The presented composition is very different from the composition of herein presented invention, due to differences in the formulation—matrix, thickening agents, solubilising agents, active materials—the composition comprises THC, which is euphoric and can cause side effects—dizziness, psychosis, etc. The anti-inflammatory COX 2 inhibitors—cannabidiolic acids—CBDA—is not listed as a key compound of the composition.

SUMMARY OF THE INVENTION

Herein presented invention relates to oleo gel composition comprising *Cannabis sativa* for the treatment and/or reduction of deep tissue join and muscle inflammation resulted from mechanical trauma of skeletal muscles or arthritis/osteoarthritis (OA). The oleo gel composition is based on *Cannabis sativa* extract comprising Cannabidiol (CBD), Cannabidiolic acid (CBDA), Cannabivarin (CBV) Cannabigerol (CB-G) (amount of phytocannabinoids—2% from total mass). The phytocannabinoids are introduced with the ratio of CBDA and CBD 1:1, 1%:1%, respectively, wherein the CBD and CBDA enriched extract is produced using an approach of supercritical extraction with $CO_2$. Following this, the Cannabis extract is mixed with extract from *Olive europaea* (Olive) Fruit (82%), *Mentha arvensis* leaf oil (0.5%), and Silica colloidal anhydrous (8.2%). Phytocannabinoids exert anti-inflammatory, anti-oxidative and bactericidal features. The synergetic effect of phytocannabinoids results in deep hydration, reduces inflammatory effect, *Mentha* oil acts as a CBD/CBDA transporter.

DETAILED DESCRIPTION OF THE INVENTION

Figure 1:
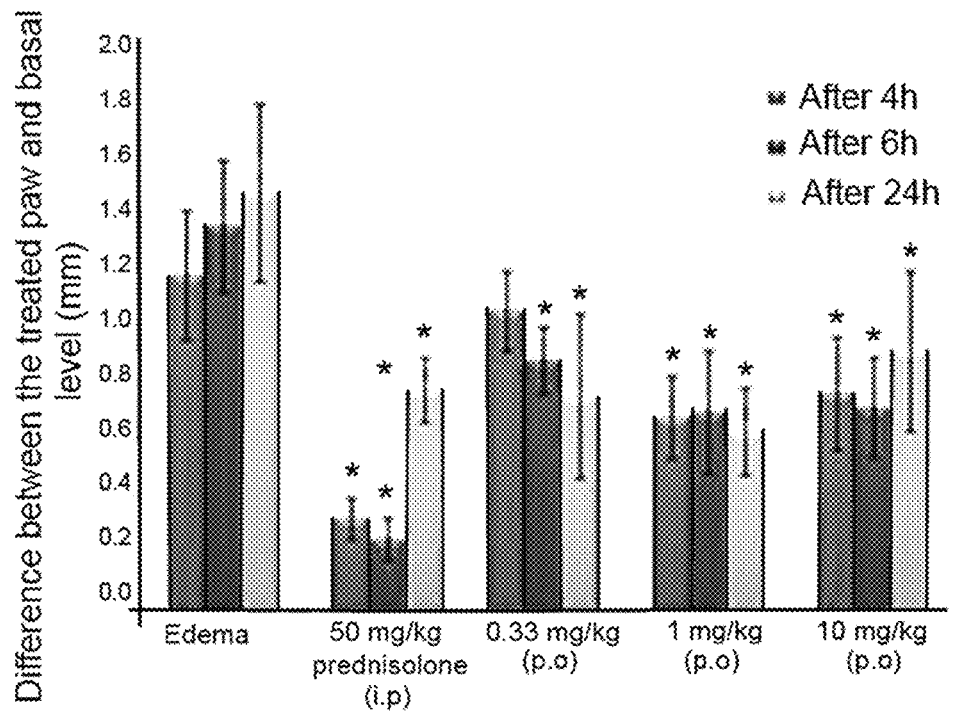
FIG. 1 Shows data presented as group averages±SN. Differences between control/edema and phytocannabinoid preparation groups are considered significant at $p<0.05$*.

Materials and Methods
Preparation of *Cannabis Sativa* Extract

Cannabis extract is produced using pulverized, dried (passive drying process for 52 hours at 35-40° C., to reach residual moisture level of approximate 10%) biomass of *Cannabis sativa* "Benico" variety which is derived from the mixture comprising upper plant parts—blossoms, and leaves. However, other non-psychotropic *Cannabis sativa* varieties can be used, where THC concentration rages from 0.0001 to 1%. The CBD and CBDA enriched lipophilic fraction (extract) is produced using an approach of supercritical extraction with $CO_2$ with the following parameters: pressure—465 bar, extraction temperature—70° C., process length—120 minutes. The CBD resin is produced by decarboxylation of CBDA resin at 160° C. for 5-6 hours.

The amount of major cannabinoids: CBD, CBDA, CBG, CBV in the cannabis extract is determined according to the ST/NAR/40 "Recommended Methods for the Identification and Analysis of Cannabis Products" (United Nations, New York, 2009). 10 mg of the resin is homogenised in the 1 mL mixture of methanol and chloroform (v/v, 9:1), for 15 min in the ultrasound bath. After centrifugation for 10 min at max g to separate insolubilities, the prepared samples were analysed using Shimadzu HPLC chromatography system with 30AC automatic injector, CTO-20AC column thermostat, DGU 20A5 vacuum degas unit, LC-30AD pump and SPD-M20A diode matrix detector. The analysed cannabinoids were fractionated in Supelco Discovery HS C18 (25×4.6 mm, 5 μm) (RP) with C18 pre-column under the isocratic elution conditions. The temperature of the column—30° C., mobile phase: acetonitrile 0.1%, flow 0.8 ml/min., separation time 30 min.; injection volume—20 μl; detection at the two channels 225 nm and 306 nm. The data was analysed by Lab Solutions software. The following internal standards were used from Cerilliant: Cannabinol, 1.0 mg/mL (C-046), Cannabidiolic acid (CBDA), 1.0 mg/mL (C-144), Cannabidivarin (CBDV), 1.0 mg/mL (C-140), Cannabigerol (CBG), 1.0 mg/mL (C-141).

Characteristics of *Cannabis sativa* extract—Protein fraction (Kjeldahl Method)—0.63%, Lipids (Soxlet Method)—96.60%, water Gravimetric Method (103 dgr centigrade)—1.73%, sum of CBD/CBDA/CBDV/CBG ~18%, where the extract comprises 80% of CBDA from the total cannabinoids, THC<0.1%.

Preparation of Tropical Composition

| Compound | Content (%) | Vendor and specifications |
|---|---|---|
| Silica colloidal anhydrous | 8.2 | — |
| *Olive europaea* fruit oil | 82 | — |
| *Mentha arvensis* leaf oil | 0.5 | — |
| Decarboxylated *Cannabis sativa* extract CBD (~20 mg/g WW) | 6% CBD | 15-18% CBD resin [Satimed] |
| Non-carboxylated *Cannabis sativa* extract CBDA (~20 mg/g WW) | 6% CBDA | 15-18% CBDA resin [Satimed] |
| Phenoxyethanol | 0.5 | — |

Initially, decarboxylated and non-carboxylated extracts of *Cannabis sativa* are mixed one by one into the pre-warmed (40° C.) *Olive europaea* (Olive) Fruit Oil followed by the addition of required amounts of *Mentha arvensis* leaf oil and Phenoxyethanol. At this point the mixing is increased up to 100 rpm and the amount of Silica colloidal anhydrous is added stepwise to reach the required amounts. The homogenisation is continued for 30-45 minutes at the temperature of 40° C. to acquire required consistency and product is filled into the required vessels.

EXAMPLES

Example 1

Experimental Procedures

The effects of two phytocannabinoid preparations (JSC SATIMED): "Preparation 1" (in which the concentration of phytocannabinoids is 40 mg/ml, extract diluted 4.5 fold with raw *Cannabis sativa* seed oil) and "Preparation 2" (10 mg/ml of phytocannabinoids, extract diluted 10 fold with raw *Cannabis sativa* seed oil), were analysed on the model of acute inflammation (paw edema) in mice. Three single doses of preparation "Preparation 1" (0.33 mg/kg, 1 mg/kg and 10 mg/kg phytocannabinoids) and one dose of "Preparation 2" (0.23 mg phytocannabinoids) were tested. The experiment was performed on 48 mice (BALB/c strain ♀, 6-7 weeks old, average weight 23 g), which were divided into 6 groups (6 mice per group), and in all of them paw edema was induced:

1 group. Edema/control—no treatment
2 group. 50 mg/kg prednisolone/control i.p.
3 group. 0.33 mg/kg phytocannabinoids "Preparation 1" p.o.
4 group. 1 mg/kg phytocannabinoids "Preparation 1" p.o.
5 group. 10 mg/kg phytocannabinoids "Preparation 1" p.o.

6 group. 0.23 mg phytocannabinoids "Preparation 2" (topical application) (i.p.—intraperitoneally, p.o.—orally)

Prior to the study, the thickness of the right hind foot of each mouse was measured by a digital micrometre (Mitutoyo, Japan). Acute inflammation (paw edema) was induced to all mice by an injection of 20 μl of 1% λ—carrageenan into their right paw. The effects of phytocannabinoids on acute inflammation (paw edema) were measured by analysing the differences between the thickness of the affected and unaffected paw. The test and control materials were administered to animals one hour after carrageenan injection. Digital micrometre measurements were carried out after 4, 6 and 24 hours of carrageenan injection.

Results: *Cannabis sativa* extract of topical composition reduces inflammation of Paw edema in mice model after oral administration and topical treatment.

Paw edema was reduced by all analysed doses of "Preparation 1". The most effective inhibition was observed at 1 mg/kg phytocannabinoid dose, which reduced the rates of paw edema (in comparison to the control group) by 43.2%-57.5% depicted in FIG. 1.

Figure 2:
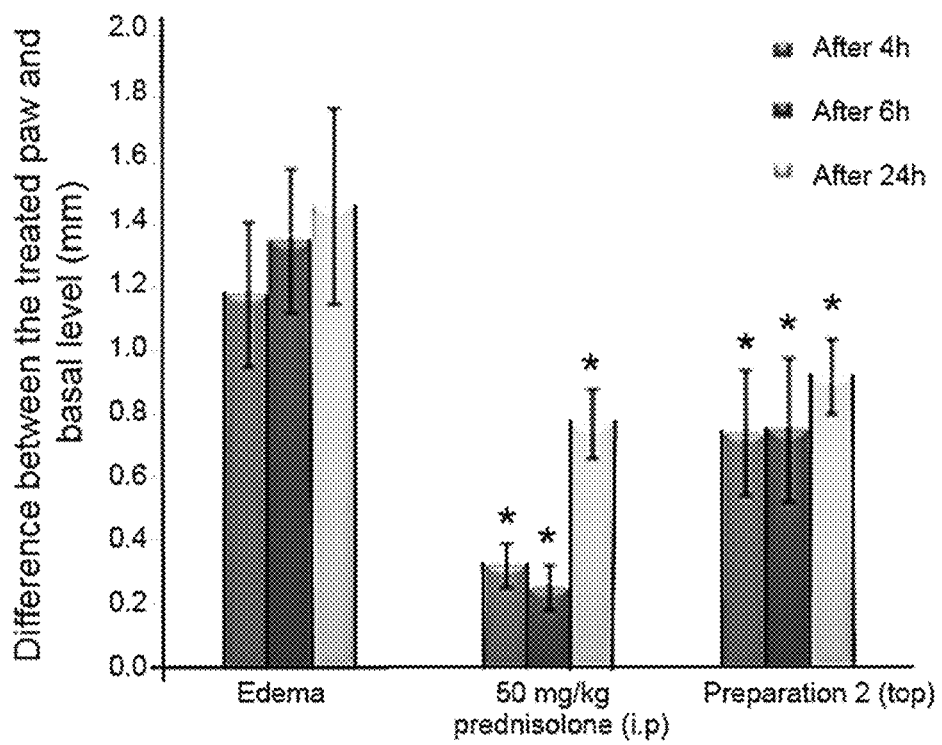
FIG. 2 Shows data presented as group averages±SN. Differences between control/edema and phytocannabinoid preparation groups are considered significant at $p<0.05$*.

Local application of preparation "Preparation 2" statistically significantly reduced paw edema (up to 44.4%) as shown in FIG. 2.

REFERENCES

1. Almekinders, L. C. 1999. "Anti-Inflammatory Treatment of Muscular Injuries in Sport. An Update of Recent Studies." *Sports Medicine (Auckland, N.Z.)* 28 (6): 383-88.
2. Baoge, L., E. Van Den Steen, S. Rimbaut, N. Philips, E. Witvrouw, K. F. Almqvist, G. Vanderstraeten, and L. C. Vanden Bossche. 2012. "Treatment of Skeletal Muscle Injury: A Review." *ISRN Orthopedics* 2012: 689012. doi:10.5402/2012/689012.
3. Bondesen, Brenda A., Stephen T. Mills, Kristy M. Kegley, and Grace K. Pavlath. 2004. "The COX-2 Pathway Is Essential during Early Stages of Skeletal Muscle Regeneration."*American Journal of Physiology. Cell Physiology* 287 (2): C475-83. doi:10.1152/ajpcell.00088.2004.
4. Fisar, Zdenek. 2009. "Phytocannabinoids and Endocannabinoids." *Current Drug Abuse Reviews* 2 (1): 51-75.
5. Fogh, Karsten, Troels Herlin, and Knud Kragballe. 1989. "Eicosanoids in Skin of Patients with Atopic Dermatitis: Prostaglandin E 2 and Leukotriene B 4 Are Present in Biologically Active Concentrations." *Journal of Allergy and Clinical Immunology* 83 (2): 450-55.
6. Hampson, A. J., M. Grimaldi, J. Axelrod, and D. Wink. 1998. "Cannabidiol and (-)Delta9-Tetrahydrocannabinol Are Neuroprotective Antioxidants." *Proc Natl Acad Sci USA* 95 (14): 8268-73.
7. Hassan, Samia, Khalil Eldeeb, Paul J. Millns, Andrew J. Bennett, Stephen P. H. Alexander, and David A. Kendall. 2014. "Cannabidiol Enhances Microglial Phagocytosis via Transient Receptor Potential (TRP) Channel Activation." *Br J Pharmacol* 171 (9): 2426-39. doi:10.1111/bph.12615.
8. Izzo, Angelo A., Francesca Borrelli, Raffaele Capasso, Vincenzo Di Marzo, and Raphael Mechoulam. 2009. "Non-Psychotropic Plant Cannabinoids: New Therapeutic Opportunities from an Ancient Herb." *Trends Pharmacol Sci* 30 (10): 515-27. doi:10.1016/j.tips.2009.07.006.
9. Li, Yong, James Cummins, and Johnny Huard. 2001. "Muscle Injury and Repair." *Current Opinion in Orthopaedics* 12 (5): 409-15.
10. Maccarrone, M., and A. Finazzi-Agro. 2003. "The Endocannabinoid System, Anandamide and the Regulation of Mammalian Cell Apoptosis." *Cell Death & Differentiation* 10 (9): 946-55.
11. Malfait, A. M., R. Gallily, P. F. Sumariwalla, A. S. Malik, E. Andreakos, R. Mechoulam, and M. Feldmann. 2000. "From the Cover: The Nonpsychoactive Cannabis Constituent Cannabidiol Is an Oral Anti-Arthritic Therapeutic in Murine Collagen-Induced Arthritis." *Proceedings of the National Academy of Sciences of the United States of America* 97 (17): 9561.doi:10.1073/pnas.160105897.
12. Nderitu, Paul, Lucy Doos, Peter W. Jones, Simon J. Davies, and Umesh T. Kadam. 2013. "Non-Steroidal Anti-Inflammatory Drugs and Chronic Kidney Disease Progression: A Systematic Review." *Family Practice* 30 (3): 247-55.doi:10.1093/fampra/cms086.
13. Neogi, Tuhina, and Yuqing Zhang. 2013. "Epidemiology of OA." *Rheumatic Diseases Clinics of North America* 39 (1): 1.doi:10.1016/j.rdc.2012.10.004.
14. Pertwee, R. G. 2008. "The Diverse CB1 and CB2 Receptor Pharmacology of Three Plant Cannabinoids: delta9-Tetrahydrocannabinol, Cannabidiol and delta9-Tetrahydrocannabivarin." *Br J Pharmacol* 153 (2): 199-215.doi:10.1038/sj.bjp.0707442.
15. Rainsford, K. D., S. C. Roberts, and S. Brown. 1997. "Ibuprofen and Paracetamol: Relative Safety in Nonprescription Dosages." *Journal of Pharmacy and Pharmacology* 49 (4): 345-76.doi:10.1111/j.2042-7158.1997.tb06809. x.
16. Ramer, Robert, Katharina Heinemann, Jutta Merkord, Helga Rohde, Achim Salamon, Michael Linnebacher, and Burkhard Hinz. 2013. "COX-2 and PPAR-γ Confer Cannabidiol-Induced Apoptosis of Human Lung Cancer Cells." *Mol Cancer Ther* 12 (1): 69-82. doi:10.1158/1535-7163.MCT-12-0335.
17. Roth, Dr Sanford H. 2012. "Coming to Terms with Nonsteroidal Anti-Inflammatory Drug Gastropathy." *Drugs* 72 (7): 873-79.doi:10.2165/11633740-000000000-00000.
18. Ryan, Duncan, Alison J. Drysdale, Carlos Lafourcade, Roger G. Pertwee, and Bettina Platt. 2009. "Cannabidiol Targets Mitochondria to Regulate Intracellular Ca2+ Levels." *J Neurosci* 29 (7): 2053-63.doi:10.1523/JNEUROSCI.4212-08.2009.
19. Samuelsson, B. 1990. "Arachidonic Acid Metabolism: Role in Inflammation." *Zeitschrift Fur Rheumatologie* 50: 3-6.
20. Schneider, Christian. 2011. "Traumeel—an Emerging Option to Nonsteroidal Anti-Inflammatory Drugs in the Management of Acute Musculoskeletal Injuries." *International Journal of General Medicine* 4: 225-34.doi: 10.2147/IJGM.S16709.
21. Schwitzer, Thomas, Raymund Schwan, Karine Angioi-Duprez, Isabelle Ingster-Moati, Laurence Lalanne, Anne Giersch, and Vincent Laprevote. 2015. "The Cannabinoid System and Visual Processing: A Review on Experimental Findings and Clinical Presumptions." *Eur Neuropsychopharmacol* 25 (1): 100-112.doi:10.1016/j.euroneuro.2014.11.002.
22. Shen, Wei, Yong Li, Ying Tang, James Cummins, and Johnny Huard. 2005. "NS-398, a Cyclooxygenase-2-Specific Inhibitor, Delays Skeletal Muscle Healing by Decreasing Regeneration and Promoting Fibrosis." *The American Journal of Pathology* 167 (4): 1105-17.doi: 10.1016/S0002-9440(10)61199-6.
23. Shen, Wei, Victor Prisk, Yong Li, William Foster, and Johnny Huard. 2006. "Inhibited Skeletal Muscle Healing 24. Shrivastava, Amit Kumar, and Aparna Pandey. 2012. "Inflammation and Rheumatoid Arthritis." *Journal of Physiology and Biochemistry* 69 (2): 335-47.doi:10.1007/s13105-012-0216-5.
25. Smith, L. L., A. Anwar, M. Fragen, C. Rananto, R. Johnson, and D. Holbert. 2000"Cytokines and Cell Adhesion Molecules Associated with High-Intensity Eccentric Exercise." *European Journal of Applied Physiology* 82 (1-2): 61-67.doi:10.1007/s004210050652.
26. Sumariwalla, Percy F., Ruth Gallily, Susanna Tchilibon, Ester Fride, Raphael Mechoulam, and Marc Feldmann. 2004. "A Novel Synthetic, Nonpsychoactive Cannabinoid Acid (HU-320) with Antiinflammatory Properties in Murine Collagen-induced Arthritis." *Arthritis & Rheumatism* 50 (3): 985-98.doi:10.1002/art.20050.
27. Takeda, Shuso. 2013. "[Medicinal chemistry and pharmacology focused on cannabidiol, a major component of the fiber-type cannabis]." *Yakugaku Zasshi: Journal of the Pharmaceutical Society of Japan* 133 (10): 1093-1101.
28. Takeda, Shuso, Koichiro Misawa, Ikuo Yamamoto, and Kazuhito Watanabe. 2008. "Cannabidiolic Acid as a Selective Cyclooxygenase-2 Inhibitory Component in Cannabis." *Drug Metab Dispos* 36 (9): 1917-21.doi:10.1124/dmd.108.020909.
29. van der Stelt, Mario, and Vincenzo Di Marzo. 2005. "Anandamide as an Intracellular Messenger Regulating Ion Channel Activity." *Prostaglandins Other Lipid Mediat* 77 (1-4): 111-22.doi:10.1016/j.prostaglandins.2004.09.007
30. U.S. Pat. No. 6,949,582B1
31. Patent US20120264818A1
32. Patent EP1186298B1

The invention claimed is:

1. A topical composition for the treatment and/or reduction of deep tissue joint and muscle inflammation resulted from mechanical trauma of skeletal muscles or arthritis/osteoarthritis (OA), the topical composition comprising:
   82% olive oil;
   about 8.2% silica colloidal anhydrous;
   about 0.5% mint oil; and
   12% *Cannabis sativa* extract,
   wherein the *Cannabis sativa* extract contains Cannabidiol (CBD), Cannabidiolic acid (CBDA), Cannabivarin (CBV), and Cannabigerol (CB-G) in an amount equal to 2% of a total mass of *cannabis* extract, the phytocannabinoids being introduced with a ratio of CBDA and CBD 1:1, 1%:1%, respectively.

2. The topical composition according to claim 1, wherein the *Cannabis sativa* extract is a non-psychotropic *Cannabis sativa* variety.

3. A method for producing a non-Newtonian fluid oleo gel composition for treatment and/or reduction of deep tissue joint and muscle inflammation resulted from mechanical trauma of skeletal muscles or arthritis/osteoarthritis (OA), the method comprising steps of:
   a) extraction of *Cannabis sativa* extract using supercritical extraction with $CO_2$ with parameters of: pressure at 465 bar, extraction temperature at 70° C., process length of 120 minutes;
   b) decarboxylation of CBDA resin for 5-6 hours to produce CBD at 160° C.; and
   c) mixing obtained decarboxylated and non-carboxylated *Cannabis sativa* extracts with olive oil, mint oil, and Silica colloidal anhydrous to achieve the gel composition comprising:
      82% olive oil;
      about 8.2% silica colloidal anhydrous;
      about 0.5% mint oil; and
      12% *Cannabis sativa* extract,
      wherein the *Cannabis sativa* extract contains Cannabidiol (CBD), Cannabidiolic acid (CBDA), Cannabivarin (CBV), and Cannabigerol (CB-G) in an amount equal to 2% of a total mass of *cannabis* extract, the phytocannabinoids being introduced with a ratio of CBDA and CBD 1:1, 1%:1%, respectively.

4. A method for relieving human pain and inflammation of deep tissues of skeletal muscles and/or joints resulted from mechanical injury/trauma and/or arthritis/osteoarthritis, the method comprising applying an effective amount of the topical composition of claim 1 to an area to be treated.

5. A pharmaceutical patch comprising a system to release active compounds in a desired location for long-term treatment, the pharmaceutical patch comprising the topical composition of claim 1.

6. The topical composition according to claim 1, wherein *Cannabis sativa* is a non-psychotropic *Cannabis sativa* of "Benico" variety.

7. The method of claim 3, wherein the *Cannabis sativa* is a non-psychotropic *Cannabis sativa* variety.

8. The method of claim 3, wherein the *Cannabis sativa* is a non-psychotropic *Cannabis sativa* of "Benico" variety.

9. The method of claim 3, wherein a concentration of the Cannabidiol (CBD) and Cannabidiolic acid (CBDA) in the non-Newtonian fluid oleo gel composition is 20 mg/g, w/w.

* * * * *